United States Patent [19]

Connolly

[11] Patent Number: 5,238,680
[45] Date of Patent: Aug. 24, 1993

[54] TANNIN EXTRACTION

[75] Inventor: David L. Connolly, Melbourne, Australia

[73] Assignee: Chem Eng Contracts Pty Ltd, Moorabbin, Australia

[21] Appl. No.: 671,866

[22] PCT Filed: Aug. 7, 1990

[86] PCT No.: PCT/AU90/00335
§ 371 Date: Apr. 2, 1991
§ 102(e) Date: Apr. 2, 1991

[87] PCT Pub. No.: WO91/01989
PCT Pub. Date: Feb. 21, 1991

[30] Foreign Application Priority Data

Aug. 8, 1989 [AU] Australia ............... PJ5648

[51] Int. Cl.$^5$ .............. A61K 35/78; B01D 11/02; C07C 69/88
[52] U.S. Cl. .............. 424/195.1; 514/783; 422/261; 560/68; 210/651; 210/195.1
[58] Field of Search .............. 424/195.1; 514/783; 422/261; 560/68; 210/651, 770, 195.1

[56] References Cited

U.S. PATENT DOCUMENTS

| 4,460,578 | 7/1984 | Cervelle | 424/195 |
| 5,043,160 | 8/1991 | Würsch | 424/195.1 |

FOREIGN PATENT DOCUMENTS

| 518703 | 1/1979 | Australia . |
| 533791 | 7/1980 | Australia . |
| 66928/86 | 1/1988 | Australia . |
| 8166387 | 3/1988 | Australia . | 424/195.1 |
| 2174386A | 11/1986 | United Kingdom . |

OTHER PUBLICATIONS

Crawford Harold B., Perry's Chemical Engineers Handbook, McGraw Hill 1984 pp. 19-73-19-86.
Abstract 97: '164739b, Manas, Adelina E., *NSTA Technol. J.*, 1982 7(1), 57-64 (Eng).
Abstract 102: 8404e, Marutzky, R., *J. Appl. Polym. Sci.: Appl. Polym. Symp.*, 1984, 40 (Wood Adhes), 91-100 (Eng).
V. Tisler et al., "Fractionation of hot water extract from Picea abies Karst. bark," *Holz als Roh-und Werkstoff*, 44, 1986, 427-431.
Abstract No. 108: 206528k (Rahman, M. D. et al.), *J. Wood Chem. Technol.*, 1988, 8(1), 111-20 (Eng.).

*Primary Examiner*—Michael G. Wityshyn
*Assistant Examiner*—Ralph Gitomer
*Attorney, Agent, or Firm*—Merchant, Gould, Smith, Edell, Welter & Schmidt

[57] ABSTRACT

Method for extracting tannins from bark and multi-stage apparatus suitable therefor. The method includes the steps of: contracting bark containing tannins with a first tannin enriched aqueous wash medium at elevated temperatures; separating the tannin-rich liquid extract by filtration including dewatering the resulting filter cake under pressure; washing the filter cake with a plurality of aqueous wash media at elevated temperatures; and separating the tannin enriched media after each washing stage by filtration including dewatering the filter cake under pressure; wherein each successive wash medium has a lower degree of tannin enrichment than the preceding wash medium.

21 Claims, 1 Drawing Sheet

TANNIN EXTRACTION

BACKGROUND OF THE INVENTION

1. Field of the Invention

The present invention relates to the extraction of tannins from natural sources and in particular to the extraction of tannins present in bark and wood extracts.

Tannins may be found in the bark and wood extracts of various varieties including wattles (acacias) and pines (pinus). Such naturally occurring tannins are polyhydroxyphenols commonly referred to as polyphenols. In pinus radiata bark for example the molecular weight of tannins can range from less than $10^3$ to more than $10^6$.

Wattle tannins are generally of lower molecular weight and lower viscosity which is generally believed to be due to the action of sugars naturally present in wattle tannins acting as viscosity reducers.

Pine tannins are generally more reactive than wattle tannins and are especially suitable for use as wood adhesives, particularly in the manufacture of plywood and particle board. Other potential applications for tannins include finger jointing wood adhesives, paper impregnation, leather tanning, dispersing clays, minerals and pigments, foundry core binding and polyurethane production.

The higher molecular weight and higher viscosity portions of tannins are useful in production of adhesives but are difficult to extract with conventional methods as they do not diffuse as readily as tannins of lower molecular weight.

2. Discussion of the Prior Art

Australian Patent Specification 533,791 discloses a method for producing a low viscosity material suitable for use in a formaldehyde-condensation adhesive which comprises subjecting a conventional aqueous extract of bark or wood to ultrafiltration and separating out that fraction which does not contain the high viscosity producing materials. There is no detailed disclosure of the method or apparatus of extraction only a reference to simple batch extraction of comminuted wood and bark with hot water at about 100° C. This conventional technique has the disadvantage however of low extraction rates.

Australian Patent Specification 569,439 also refers to the low yields of the known aqueous extraction process and to the difficulties of formulating adhesives from 100° C. aqueous extracts. This specification provides also a method for producing a relatively low viscosity tannin extract involving separation and treatment of the high molecular weight material with one or more sulphite compounds to reduce the molecular weight prior to recombining with the low molecular weight material.

Neither of these methods teach a method or apparatus for increasing the extraction yield.

Australian Patent Specification 579,783 also recognises the difficulties which have been encountered with conventional extraction techniques. The difficulties which have been encountered are attributed primarily to excessive viscosity of the extracts and the difficulty in obtaining uniformity in product quality.

Specification 579,783 teaches a method for recovering tannin extract which comprises subjecting bark and/or wood to a first stage hot aqueous tannin extraction process, to obtain a first stage tannin extract. This is followed by a second stage hot aqueous extraction process at a higher pH than the first stage then recombining the first and second stage extracts. The specification further teaches the separation of high molecular weight material and treatment thereof with one or more sulphite compounds to reduce the molecular weight.

The use of a two stage process and the introduction of sulphites result in a more complex extraction method and increases the risk of environmental contamination.

In Australian Patent Specification 518,703 the point is made that although it is a relatively simple matter to prepare aqueous phenolic extracts from bark in the laboratory the phenolic materials contained in the extracts are very reactive and considerable difficulty is experienced in preventing or minimising premature reactions which make the extracts obtained less useful. This specification refers to a hot water extraction process as not favoured for use with most bark species principally on account of the uneconomically low yields of extractives obtained.

Specification 518,703 teaches a method of treating an aqueous phenolic bark extract which involves adjusting the pH above 7 maintaining the extract temperature above 49° C. for a period of up to 90 minutes and adjusting the pH of the extract to below pH 7. This method requires close monitoring of the extract and addition of chemicals to adjust pH. Moreover, the treatment method proposed is independent of the particular method used to derive the extract from the bark and accordingly does not provide increased extraction yields.

Accordingly a need exists for a novel method and apparatus for the more efficient extraction of tannins from bark.

SUMMARY OF THE INVENTION

It is an object of the present invention to provide, in one embodiment, a novel method for extracting tannins from bark.

It is a further object of the present invention to provide, in another embodiment, a novel apparatus for extracting tannins from bark.

The present invention provides in one embodiment a method for extracting tannins from bark including the steps of:

contacting bark containing tannins with a first tannin enriched aqueous wash medium at elevated temperatures;

separating the tannin-rich liquid extract by filtration including dewatering the resulting filter cake under pressure;

washing the filter cake with a plurality of aqueous wash media at elevated temperatures; and separating the tannin enriched media after each washing stage by filtration including dewatering the filter cake under pressure;

wherein each successive wash medium has a lower tannin content than the preceding wash medium.

According to a further embodiment the invention also provides a multi-stage apparatus for extracting tannin from bark comprising an extraction tank for slurrying fresh bark with a tannin enriched wash medium to effect primary extraction;

a filter for filtering the slurry after primary extraction and for dewatering the resulting filter cake under pressure;

at least one wash liquor holding tank for providing a tannin enriched liquor for washing a filter cake in the filter;

a source of hot water for providing a final medium for washing the filter cake in the filter; and pumping means for moving the slurry and/or liquid media between the tanks and the filter wherein the filter is adapted for dewatering the filter cake under pressure between each separation and/or wash step.

The invention may also include a tannin rich recycle circuit. In this arrangement the tannin rich stream flowing from the filter may be separated whereby a portion thereof is recycled preferably via a holding tank or header tank to facilitate forming a pumpable slurry with fresh bark and whereby the remainder thereof is recovered from the system as a tannin rich extract. The removed portion may optionally undergo concentration whereby to form a concentrated extract.

The bark provided as a raw material for use according to the invention is preferably comminuted before introduction into the extraction tank. The introduced bark may be milled bark and is preferably finely milled so as to facilitate solid liquid contact and thereby improve the extraction rate. As higher molecular weight tannins do not readily diffuse it is preferable if only a smaller percentage, preferably not more than 5% of the bark is greater than 1 mm in size. In a typical run of mill bark sample at least 20% of the sample may be less than 125 microns.

A typical distribution for run of mill pinus radiata bark suitable for use in accordance with the present invention is as follows:

| | |
|---|---|
| Less than 125 microns | 43% |
| More than 125 microns | 19.5% |
| More than 212 microns | 16.9% |
| More than 355 microns | 13.6% |
| More than 600 microns | 3.9% |
| More than 1 mm | 0.5% |

Although the present invention is particularly suitable for application to pinus radiata bark it is to be appreciated that the invention may also be applied to other barks and to other tannin containing wood products.

The filter provided in accordance with the invention is preferably a pressure filter of the plate and frame type. Preferably the filter incorporates the means for dewatering the filter cake under pressure. It is to be appreciated that the filtration and the dewatering may occur simultaneously. In some cases a degree of filtering may occur as the slurry is pumped into the filter and further dewatering may occur after the increased pressure is applied.

It is important for efficient operation of the invention that the dewatering of the filter cake after separation of each liquid extract is as complete as possible. Although tannins dissolve fairly readily in hot water it has been found that moist bark such as the bark residue after filtration can retain more than 100% or even 150% and typically around 200% of moisture by weight of dry bark. If such moisture is not minimised a considerable amount of dissolved tannin will not be separated into the liquid extracts. It is particularly preferred for dewatering to reduce the moisture content of the filter cake to less than 100% or if possible 50% by weight of dry bark.

It has been found particularly preferable if the filter applies a pressure of at least 10 bar and preferably a pressure in the range of 12 to 16 bar to the filter cake during dewatering.

A fully automatic pressure filter is preferred for use in accordance with the present invention and it has been found that a filter with a diaphragm pressing system is particularly suitable for use in the present invention. One such filter which we have found particularly suitable is the Larox pressure filter.

The primary extraction of tannins from comminuted bark may be conducted in an extraction tank. The bark and wash liquor may be slurried in the extraction tank at elevated temperatures. Preferably the tannin enriched wash medium is at a temperature of at least 60° C. and most preferably between 90° and 100° C. when brought into contact with the bark.

The present invention operates on a counter current multistage washing sequence wherein each successive wash medium has a lower tannin content than the preceding wash medium. The final wash medium is preferably water having no tannin enrichment.

It has been found convenient if each wash medium is stored in a holding tank at elevated temperatures preferably above 60° C. and most preferably between 90° and 100° C. between each wash cycle. Accordingly it is preferred if each holding tank has heating means and/or insulation associated therewith.

It has been found that the method provided by the present invention gives improved results if the milled bark and enriched wash liquor are slurried in the extraction tank at elevated temperatures for an ageing period prior to initial separation in the filter. An ageing period of between 10 minutes and 1 hour, preferably between 15 minutes and 45 minutes and most preferably between 20 minutes and 40 minutes has been found effective in increasing the rate of extraction of tannins in accordance with the invention.

To avoid the filter lying idle during the ageing period a second extraction tank may be provided in accordance with the invention whereby the slurried bark and wash liquor in the second tank may undergo ageing while the contents of the first tank is undergoing separation and washing and vice versa.

The apparatus provided in accordance with the present invention may also include agitating means for retaining the slurry in suspension in the extraction tank. Preferably the apparatus also includes insulation means for retaining liquids in the system at elevated temperatures.

As tannins tend to chelate with the iron in mild steel causing darkening of the colour of the extract and blackening of the equipment it is preferred if the apparatus of the invention is constructed from stainless steel, plastics or other inert materials.

The source of hot water may be a holding tank adapted to be refilled with water as required and preferably adapted for heating water to the desired elevated temperature.

Preferably the bark undergoes a plurality of washing stages following initial separation of the slurry. There may be at least 2 preferably 3 and most preferably between 2 and 4 and not more than 5 washing stages following initial separation of the slurry. The wash medium used in each stage has a lower tannin content than that of the preceding stage. The final wash medium may be unenriched water.

For use in particle board manufacture a solids content of at least 30% tannin and preferably from 35 to 45% is preferred in the final extract. The tannin rich extract from the filter may accordingly be passed through an evaporator to form a concentrated extract of the desired concentration. Conventional evaporators such as falling film, forced circular or plate evaporators are suitable for use in accordance with the invention.

The extraction method and apparatus provided according to the invention has been found to be efficient and adaptable in that by varying the amount of wash liquor employed the tannin concentration in the final extract may vary. For example if the volume of wash liquor is increased the volume of extract will increase but the concentration will reduce.

The spent bark after undergoing tannin extraction in accordance with the invention may be used as fuel or for horticultural or other applications.

A preferred embodiment of the invention will now be described in relation to the drawing.

DETAILED DESCRIPTION

Figure 1:
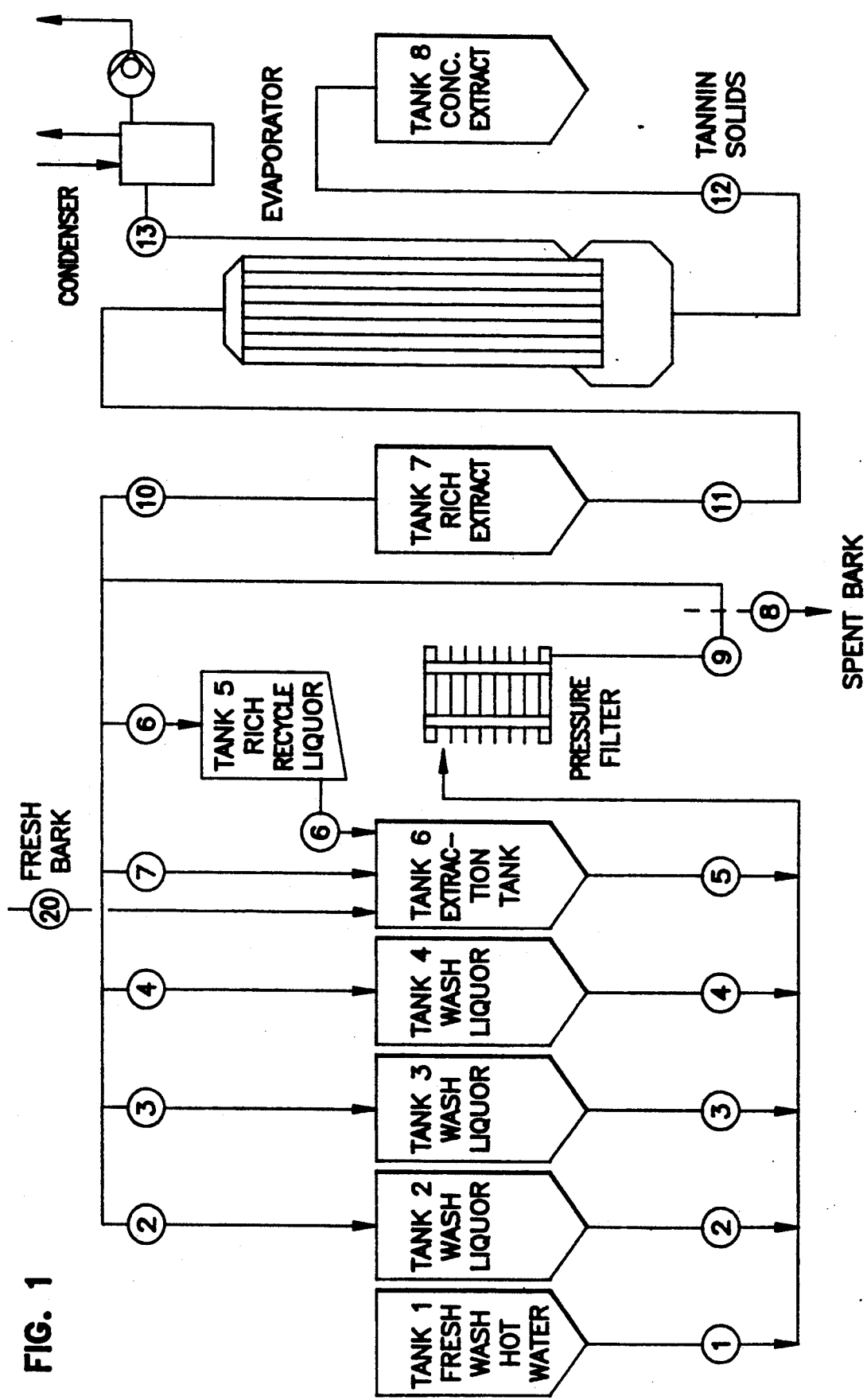
FIG. 1 comprises a schematic representation of a tannin extraction apparatus in accordance with the present invention.

Fresh wash hot water is introduced into the apparatus via holding tank 1. Faucet means is provided for topping up tank 1 with fresh water. Tank 1 is also provided with heating means to facilitate water being drawn from tank 1 at elevated temperatures preferably between 95° and 100° C.

Extraction of tannin according to the present invention is achieved by successive washing with progressively more dilute solutions at elevated temperatures with filtration and dewatering between each washing stage until the strength of the enriched solutions decreases below a predetermined level. The hot water from tank 1 comprises the final wash solution.

Holding tanks 2 to 5 progressively hold tannin enriched liquors of increasing concentration. Each tank may be insulated and/or may contain heating means to facilitate wash media being drawn from the tank at an elevated temperature preferably in the range of from 95° to 100° C.

Tank 6 comprises an extraction tank for slurrying fresh comminuted bark with the wash liquor from tank 5 which is a tannin enriched wash medium.

In the operation of the apparatus shown in FIG. 1 according to the method provided by the present invention finely comminuted bark a majority of which is preferably −1 mm in size, is added to extraction tank 6. An extraction solution being tannin enriched wash liquors from tanks 4 and 5 is added to tank 6. After the bark and extraction solution is aged in tank 6 under agitation at elevated temperature for a period of not more than 1 hour and preferably for a period of from 20 to 40 minutes, the slurry is pumped to the pressure filter in which the final rich liquor is separated from the bark. The final rich liquor which may contain approximately 10 to 15% tannin depending upon the amount of wash water introduced per cycle is divided into two streams. One stream is passed via paths 9 and 6 to rich recycle liquor tank 5. This stream forms a rich liquor recycle circuit within the apparatus of the invention. The other stream which may comprise the balance of the rich liquor extract from the pressure filter passes through rich extract holding tank 7 via paths 10 and 11 to be concentrated in the evaporator. The concentrated extract from the evaporator may have a tannin solids content of at least 30% and preferably around 40%. The extract is passed to holding tank 8 via path 12. The removed moisture may pass through a condensor via path 13 before discharge from the system.

The filter cake remaining in the pressure filter is washed by a wash liquor from tank 4 which in a typical example may increase from approximately 2-3% tannin as it proceeds via path 4 to the filter to approximately 12% tannin as it proceeds via path 6 to holding tank 5 and subsequently extraction tank 6.

Holding tank 5 acts as a header tank for enriched wash liquor and is used for withholding the wash liquor while wash liquor from a preceding cycle is ageing with bark in tank 6 and being fed into the filter. Holding tank 5 accordingly forms part of a rich liquor recycle circuit.

It is to be appreciated that the rich recycle liquor in tank 5 and rich extract in tank 7 have the same tannin content as tanks 5 and 7 are filled by a separation of the tannin rich stream flowing from the filter via path 9. The internal rich liquor recycle so formed increases the amount of liquid in tank 6 preferably to a level of 5 parts liquid to 1 part bark which facilitates forming a pumpable slurry with the bark.

Tank 5 accordingly acts as a holding tank for that proportion of the filter extract to be recycled. It is preferred to use a holding tank rather than to introduce the recycle stream directly into tank 6 as the extract to be recycled in any particular cycle may commence flowing from the filter along paths 9 and 6 before tank 6 is emptied of slurry.

After separation of the liquid phase from tank 6 in the pressure filter to provide the filter cake, the cake may be washed successively by the wash liquors in tanks 4, 3, 2 and 1 via paths 4, 3, 2 and 1 respectively.

In a typical arrangement the wash liquors held in tanks 4, 3 and 2 may respectively hold approximately 2-3, 1 and 0.5% tannin.

Although not shown in FIG. 1 a second extraction tank may be provided to enable ageing of a bark and concentrated wash liquor slurry in one tank while material from the other extraction tank is undergoing multistage washing. The second extraction tank may be filled with enriched wash media from the pressure filter via an alternative path 7 and from wash liquor tank 5 via an alternative path 6.

Fresh bark is added to the system via path 20 to extraction tank 6.

By finely milling or otherwise comminuting the bark prior to addition to extraction tank 6 via path 20 the tannin extractions facilitated and a pumpable slurry is formed.

It may be necessary to pre-dry the bark to restrain tannin polymerisation through a composting action which may occur if the bark is left in large moist stockpiles. Similarly, if the bark is not pre-dried prior to addition to the system excessive moisture which may be up to 120% or more by weight would effectively dilute the rich extract proceeding via path 10 to tank 7 and thereby reduce the effectiveness of the invention.

If drying is required prior to addition of fresh bark via path 20 a simple hot air dryer would be suitable. Such a dryer may be fired at least partly by spent bark removed from the system via path 8.

Preferably each of tanks 1 to 6 is insulated and/or heated and all pipes are preferably lagged whereby to maintain all liquids upstream of rich extract tank 7 at elevated temperatures.

Older butt log bark has a higher tannin content than younger strand bark however the younger bark generally contains tannins of a lower molecular weight and is therefore easier to extract.

The nature of the bark accordingly determines the molecular weight of the tannins produced in accordance with the invention. One of the advantages provided by the present invention is that the extraction of naturally occurring tannins from bark may be carried out without the addition of any reagents other than water. However, additives may be introduced into the system for example if the molecular weight characteristics of the final product are to be altered. Additives may be added to extraction tank 6 when fresh bark is introduced or may be added elsewhere into the system.

A small amount of phenol, preferably not more than 5% and most preferably around 3% on tannin solids may be added to the pre-concentrate to reduce concentrate viscosity. Such an additive addition may retard mold growth in the concentrated extract which may otherwise be encouraged by the presence of sugars, gums, etc. in the extract.

The spent bark after the final washing and dewatering stage may be removed from the filter via path 8 and may be used for nursery and horticultural applications. The spent bark may also be a suitable fuel for example to provide hot gases for drying fresh bark thereby conserving energy within the system.

The method and apparatus provided by the present invention provides a mechanical extraction method which avoids degrading the tannin molecules by chemical attack and also provides for high tannin extraction efficiencies without using large quantities of liquid. The low water/dry bark ratio preferably in the vicinity of 3:1 results in a high concentration extract preferably in the region of 10 to 15%. The use of a water/dry bark ratio in the region of 3.5:1 would generally not be sufficient to form a pumpable slurry suitable for extraction however by recycling a portion of the rich extract this can be achieved in accordance with the present invention. The present invention accordingly facilitates the production of a high concentration tannin extract without the need for extensive evaporation. Further, by using only hot water for the extraction no potentially injurious chemical salts are introduced.

Bark can be rather bulky and difficult to transport. The present invention has the added advantage that movement of bark is kept to a minimum.

While it has been convenient to describe the invention herein in relation to particularly preferred embodiments, it is to be appreciated that other constructions and arrangements are also considered as falling within the scope of the invention. Various modifications, alterations, variations and/or additions to the constructions and arrangements described herein are also considered as falling within the scope and ambit of the present invention.

I claim:

1. A method for extracting tannins from tannin-containing bark; said method comprising the steps of:
   (a) contacting tannin-containing bark with an amount of a first tannin-enriched aqueous wash medium for a length of time sufficient to extract the tannins to form a slurry of a tannin-rich liquid extract and extracted bark; said tannin-enriched aqueous wash medium having a temperature within the range of 60°–100° C.;
   (b) separating the tannin-rich liquid extract from the extracted bark by pressure filtration; said step of separating comprising:
      (i) filtering the tannin-rich liquid extract from the extracted bark to form a filter cake of extracted bark and retained tannin-rich liquid; and
      (ii) dewatering the resulting filter cake under a sufficient pressure to decrease the amount of retained tannin-rich liquid in the filter cake;
   (c) subjecting the filter cake to two subsequent washing and separating stages, wherein:
      (i) each washing stage comprises washing the filter cake with an amount of a tannin-enriched aqueous wash medium having a temperature of 60°–100° C. to extract therein tannin remaining in the filter cake and to form a tannin-rich liquid extract; said tannin-enriched aqueous wash medium having a lower degree of tannin enrichment than each previous tannin-enriched aqueous wash medium; and
      (ii) each separating stage comprises separating the tannin-rich liquid extract from the filter cake after each washing step by pressure filtration; said step of separating comprising:
         (A) filtering the tannin-rich liquid extract from the filter cake; and
         (B) dewatering the filter cake under a sufficient pressure to decrease the amount of retained tannin-rich liquid in the filter cake; and
   (d) collecting the tannin-rich liquid extract resulting from each washing and separating stages.

2. The method according to claim 1, further comprising a step of washing the filter cake with water after the step of subjecting the filter cake to two subsequent washing and separating stages to extract therein tannin remaining in the filter cake; said water having a temperature within the range of 60° C. to about 100° C. and containing no tannins.

3. The method according to claim 1, wherein the first tannin-enriched aqueous wash medium contains a portion of the tannin-rich liquid extract.

4. The method according to claim 1, wherein the tannin-rich liquid extract is subjected to concentration by evaporation to form a concentrated extract, 5. The method according to claim 1, where the tannin-containing bark comprises Pinus Radiata bark.

6. The method according to claim 1, wherein the tannin-containing bark is comminuted before contact with the first tannin-enriched aqueous wash medium.

7. The method according to claim 6, wherein no more than 5% of the tannin-containing bark is greater than about 1 mm in any dimension.

8. The method according to claim 1, wherein each step of dewatering the filter cake is conducted under a pressure of at least about 10 bar to about 16 bar.

9. The method according to claim 1 wherein the tannin-containing bark and the first tannin-enriched aqueous wash medium are slurried at a temperature within the range of about 60° to 100° C. for a period of 10 minutes to 1 hour.

10. The method according to claim 1, wherein the filter cake is subjected to two to four subsequent washing and separating stages.

11. The method according to claim 10, wherein each washing and separating stage occurs within a filter without displacement of the filter cake from the filter.

12. A method for extracting tannins from tannin-containing bark; said method comprising the steps of:
   (a) contacting tannin-containing bark with an amount of a first tannin-enriched aqueous wash medium at a temperature of 60°–100° C. for a length of time sufficient to extract the tannins to form a slurry of a first tannin-rich liquid extract and extracted bark;

(b) separating the first tannin-rich liquid extract from the extracted bark; said step of separating comprising:
  (i) filtering the first tannin-rich liquid extract from the extracted bark with a pressure filter to form a filter cake of extracted bark and retained tannin-rich liquid; and
  (ii) dewatering the resulting filter cake under a pressure within the range of about 10 bar to a maximum pressure that the presure filter can withstand to decrease the amount of retained tannin-rich liquid in the filter cake;

(c) washing the filter cake with an amount of a second tannin-enriched aqueous wash medium at a temperature of 60°–100° C. to extract the tannins to form a second tannin-rich liquid extract; said second tannin-enriched aqueous wash medium having a lower degree of tannin enrichment than said first tannin-enriched aqueous wash medium;

(d) separating the second tannin-rich liquid extract from the filter cake; said step of separating comprising:
  (i) filtering the second tannin-rich liquid extract from the filter cake with the pressure filter; and
  (ii) dewatering the filter cake under a pressure within the range of about 10 bar to a maximum pressure that the pressure filter can withstand to decrease the amount of retained tannin-rich liquid in the filter cake;

(e) washing the filter cake with an amount of a third tannin-enriched aqueous wash medium at a temperature of 60° to 100° C. to extract the tannins to form a third tannin-rich liquid extract; said third tannin-enriched aqueous wash medium having a lower degree of tannin enrichment than said second tannin-enriched aqueous wash medium;

(f) separating the third tannin-rich liquid extract from the filter cake; said step of separating comprising:
  (i) filtering the third tannin-rich liquid extract from the filter cake with the pressure filter; and
  (ii) dewatering the filter cake under a pressure within the range of about 10 bar to a maximum pressure that the pressure filter can withstand to decrease the amount of retained tannin-rich liquid in the filter cake;

(g) washing the filter cake with an amount of water containing no tannin therein at a temperature within the range of 60° C. to 100° C. to extract the tannins to form a final liquid extract; and (h) separating the final liquid extract from the filter cake; said step of separating comprising:
  (i) filtering the final liquid extract from the filter cake with a pressure filter; and
  (ii) dewatering the filter cake under a pressure within the range of about 10 bar to a maximum pressure that the pressure filter can withstand to decrease the amount of retained liquid in the filter cake; and (i) collecting the first tannin-rich liquid extract, second tannin-rich liquid extract, third tannin-rich extract, and final tannin-rich extract.

13. The method according to claim 12, wherein the pressure is within the range of about 10 bar to about 16 bar.

14. An apparatus for extracting tannins from tannin-containing bark comprising:
  (a) a first extraction tank for slurrying tannin-containing bark with a tannin-enriched aqueous wash medium to form a slurry of a tannin-rich liquid extract and extracted bark, said tank having a means for adding the tannin-containing bark, a means for adding the tannin-enriched aqueous wash medium, and a means for discharging the slurry;
  (b) a pressure filter connected to the means for discharging the slurry for fitering the discharge slurry to separate the tannin-rich liquid extract from the extracted bark to form a filter cake and to dewater the filter cake, said pressure filter having a means for applying pressure on the filter cake;
  (c) one wash liquor holding tank connected to the pressure filter for providing a tannin-enriched aqueous wash medium for washing the filter cake on the filter to form a tannin-rich liquid extract;
  (d) a source of water connected to the pressure filter for providing a final medium for washing the filter cake in the filter to form a tannin-rich liquid extract;
  (e) a tannin-rich extract collection tank for holding the tannin-rich liquid extracts flowing from the pressure filter and connected to the pressure filter; and
  (f) pumping means coupled to the tanks and the pressure filter for moving the slurry and the liquid media between the tanks and the pressure filter.

15. An apparatus according to claim 14, wherein the extraction tank includes agitating means for retaining the slurry in suspension.

16. An apparatus according to claim 14 further comprising a tannin-rich recycle circuit connected to the pressure filter and the extraction tank and adapted for separating a tannin-rich stream flowing from the pressure filter and for recycling a portion of the stream to the extraction tank.

17. An apparatus according to claim 14 in which the means for applying pressure on the filter cake applies a pressure within the range of about 10 bar to a maximum pressure that the pressure filter can withstand.

18. An apparatus according to claim 17, wherein the means for applying pressure on the filter cake applies a pressure within a range of about 10 bar to about 16 bar.

19. An apparatus according to claim 14, further comprising a second extraction tank for slurrying and aging tannin-containing bark and a tannin-enriched aqueous wash medium while the contents of the first extraction tank undergo separation and washing, said second extraction tank having means for adding tanning-containing bark, a means adding a tannin-enriched aqueous wash medium, and a means for discharging the slurry connected to the pressure filter.

20. The apparatus according to claim 14, further comprising three wash liquor holding tanks connected to the pressure filter for providing wash media of successively lower tannin contents.

21. An apparatus according to claim 14 further comprising an evaporator connected to the tannin-rich extract collection tank and adapted to form a concentrated extract from the tannin-rich liquid extract.

* * * * *